United States Patent
Kentin et al.

(10) Patent No.: US 11,642,081 B2
(45) Date of Patent: May 9, 2023

(54) ELECTRODE HEADSET

(71) Applicant: X Development LLC, Mountain View, CA (US)

(72) Inventors: Rhoda Jill Kentin, Oakland, CA (US); Haden Cory, San Francisco, CA (US); Gabriella Levine, San Francisco, CA (US)

(73) Assignee: X Development LLC, Mountain View, CA (US)

(*) Notice: Subject to any disclaimer, the term of this patent is extended or adjusted under 35 U.S.C. 154(b) by 466 days.

(21) Appl. No.: 16/780,449

(22) Filed: Feb. 3, 2020

(65) Prior Publication Data

US 2020/0245933 A1 Aug. 6, 2020

Related U.S. Application Data

(60) Provisional application No. 62/799,961, filed on Feb. 1, 2019.

(51) Int. Cl.
*A61B 5/291* (2021.01)
*A61B 5/00* (2006.01)
*A61B 5/16* (2006.01)

(52) U.S. Cl.
CPC ............ *A61B 5/6803* (2013.01); *A61B 5/165* (2013.01); *A61B 5/291* (2021.01);
(Continued)

(58) Field of Classification Search
CPC ....... A61B 5/6803; A61B 5/165; A61B 5/291; A61B 2562/0209; A61B 2562/043; A61B 2562/046; A61B 2562/225
See application file for complete search history.

(56) References Cited

U.S. PATENT DOCUMENTS 3,998,213 A 12/1976 Price
4,928,696 A 5/1990 Henderson et al.
(Continued)

FOREIGN PATENT DOCUMENTS

AU 2011244986 11/2011
AU 2014240373 10/2014
(Continued)

OTHER PUBLICATIONS trans-cranial.com [online], "10/20 System Positioning Manual", Trans Cranial Technologies, Ldt, 2012, [retrieved on Jan. 23, 2019], retrieved from: URL<https://www.trans-cranial.com/docs/10_20_pos_man-v1_0_pdf.pdf> 20 pages.

*Primary Examiner* — Eugene T Wu
(74) *Attorney, Agent, or Firm* — Fish & Richardson P.C.

(57) ABSTRACT

In general, innovative aspects of the subject matter described in this specification can be embodied in an electrode headset and methods of using an electrode headset. An exemplary electrode headset includes a head covering, an electrode assembly, and a plurality of electrodes. The head covering has a plurality of holes and the electrode assembly includes a plurality of first connectors arranged to align with the plurality of holes of the head covering. Each electrode has a second connector configured to releasably mate with one of the first connectors of the electrode assembly through one of the plurality of holes of the head covering.

15 Claims, 7 Drawing Sheets

(52) U.S. Cl.
CPC . *A61B 2562/0209* (2013.01); *A61B 2562/043* (2013.01); *A61B 2562/046* (2013.01); *A61B 2562/225* (2013.01)

(56) References Cited

U.S. PATENT DOCUMENTS

| | | | |
|---|---|---|---|
| 4,967,038 A * | 10/1990 | Gevins | A61B 5/0017 600/383 |
| 5,293,867 A | 3/1994 | Oommen | |
| 5,800,351 A | 9/1998 | Mann | |
| 6,161,030 A | 12/2000 | Levendowski et al. | |
| 7,551,952 B2 | 6/2009 | Gevins et al. | |
| 8,472,120 B2 | 6/2013 | Border et al. | |
| 8,477,425 B2 | 7/2013 | Border et al. | |
| 8,482,859 B2 | 7/2013 | Border et al. | |
| 8,488,246 B2 | 7/2013 | Border et al. | |
| 9,128,281 B2 | 9/2015 | Osterhout et al. | |
| 9,182,596 B2 | 11/2015 | Border et al. | |
| 9,229,227 B2 | 1/2016 | Border et al. | |
| 9,254,099 B2 | 2/2016 | Connor | |
| 9,341,843 B2 | 5/2016 | Border et al. | |
| 9,442,100 B2 | 9/2016 | Connor | |
| 9,451,899 B2 | 9/2016 | Ritchey et al. | |
| 9,529,385 B2 | 12/2016 | Connor | |
| 9,536,449 B2 | 1/2017 | Connor | |
| 9,675,292 B2 | 6/2017 | Fadem | |
| 9,907,473 B2 | 3/2018 | Tran | |
| 10,046,229 B2 | 8/2018 | Tran et al. | |
| 10,076,279 B2 | 9/2018 | Nahum | |
| 2005/0197756 A1 | 9/2005 | Taylor et al. | |
| 2007/0093706 A1 | 4/2007 | Gevins et al. | |
| 2007/0225585 A1 | 9/2007 | Washbon et al. | |
| 2009/0088619 A1 | 4/2009 | Turner et al. | |
| 2009/0105576 A1 | 4/2009 | Do et al. | |
| 2010/0036275 A1 | 2/2010 | Alkire | |
| 2010/0125190 A1 * | 5/2010 | Fadem | A61B 5/6814 600/383 |
| 2011/0098593 A1 | 4/2011 | Low et al. | |
| 2011/0213664 A1 | 9/2011 | Osterhout et al. | |
| 2011/0214082 A1 | 9/2011 | Osterhout et al. | |
| 2012/0235884 A1 | 9/2012 | Miller et al. | |
| 2012/0235885 A1 | 9/2012 | Miller et al. | |
| 2012/0235887 A1 | 9/2012 | Border et al. | |
| 2012/0235900 A1 | 9/2012 | Border et al. | |
| 2012/0236030 A1 | 9/2012 | Border et al. | |
| 2012/0236031 A1 | 9/2012 | Haddick et al. | |
| 2012/0242678 A1 | 9/2012 | Border et al. | |
| 2012/0242698 A1 | 9/2012 | Haddick et al. | |
| 2012/0249797 A1 | 10/2012 | Haddick et al. | |
| 2014/0143064 A1 | 5/2014 | Tran | |
| 2015/0011857 A1 | 1/2015 | Henson et al. | |
| 2015/0112153 A1 | 4/2015 | Nahum | |
| 2015/0126873 A1 | 5/2015 | Connor | |
| 2015/0257674 A1 | 9/2015 | Jordan et al. | |
| 2015/0282760 A1 | 10/2015 | Badower et al. | |
| 2016/0187654 A1 | 6/2016 | Border et al. | |
| 2016/0209648 A1 | 7/2016 | Haddick et al. | |
| 2016/0354005 A1 | 12/2016 | Oakley et al. | |
| 2017/0123495 A1 | 5/2017 | Leuthardt et al. | |
| 2017/0143228 A1 | 5/2017 | Leuthardt, Jr. et al. | |
| 2017/0173262 A1 | 6/2017 | Veltz | |
| 2017/0252534 A1 | 9/2017 | Nofzinger | |
| 2018/0239430 A1 | 8/2018 | Tadi et al. | |
| 2018/0271444 A1 | 9/2018 | Floyd | |
| 2018/0307314 A1 | 10/2018 | Connor | |
| 2019/0282168 A1 | 9/2019 | Feiner | |
| 2020/0281530 A1 | 9/2020 | Yee | |

FOREIGN PATENT DOCUMENTS

| | | |
|---|---|---|
| CA | 2963061 | 11/2015 |
| CN | 102460347 | 5/2012 |
| CN | 102906623 | 1/2013 |
| CN | 107106048 | 8/2017 |
| CN | 104768455 | 1/2018 |
| CN | 109804331 | 5/2019 |
| CN | 110234273 | 9/2019 |
| CN | 110558978 | 12/2019 |
| EP | 2698099 | 10/2018 |
| EP | 3592225 | 1/2020 |
| FR | 3028743 | 5/2016 |
| JP | 6332709 | 5/2018 |
| KR | 20170129689 | 11/2017 |
| RU | 31944 U1 | 9/2003 |
| RU | 2230483 | 6/2004 |
| RU | 2447871 | 4/2012 |
| TW | 201825045 | 11/2017 |
| WO | WO2008109694 | 9/2008 |
| WO | WO2008109699 | 9/2008 |
| WO | WO2012037290 | 3/2012 |
| WO | WO2012170816 | 12/2012 |
| WO | WO2014150199 | 9/2014 |
| WO | WO2007138598 | 6/2016 |
| WO | WO2017201088 | 11/2017 |
| WO | WO2018091823 | 5/2018 |
| WO | WO2018162482 | 9/2018 |
| WO | WO2019108968 | 6/2019 |

* cited by examiner

ELECTRODE HEADSET

CROSS-REFERENCE TO RELATED APPLICATION

This application claims the benefit under 35 U.S.C. § 119(e) of U.S. Patent Application No. 62/799,961, entitled "Electrode Headset," filed Feb. 1, 2019, which is incorporated herein by reference in its entirety.

TECHNICAL FIELD

This disclosure generally relates to wearable electrodes.

BACKGROUND

Electroencephalography is an electrophysiological monitoring method to record electrical activity of the brain. Electrical activity can be monitored using an electrode headset that is positioned on a user's head so that electrodes are positioned along the scalp. Electrode headsets are commonly disconnected from an analysis system and sanitized between users.

SUMMARY

This disclosure describes an electrode headset for use with electrical signal analysis systems such as electroencephalogram (EEG) systems and/or other bioamplification systems and methods for using the headset. The electrode headset includes an electrode assembly that is configured to be paired with disposable or washable heads coverings and electrodes.

In general, innovative aspects of the subject matter described in this specification can be embodied in an electrode headset that includes a head covering, an electrode assembly, and a plurality of electrodes. The head covering has a plurality of holes and the electrode assembly includes a plurality of first connectors arranged to align with the plurality of holes of the head covering. Each electrode has a second connector configured to releasably mate with one of the first connectors of the electrode assembly through one of the plurality of holes of the head covering.

Another general aspect can be embodied in an electrode headset that includes a head covering, an electrode assembly, and a plurality of electrodes. The head covering has a plurality of holes and the electrode assembly includes a plurality of electrode connectors arranged to align with the plurality of holes of the head covering. The electrodes are releasably coupled to the connectors of the electrode assembly through the plurality of holes of the head covering, where respective connections between the electrodes and the connectors capture a portion of the head covering therebetween attaching the head covering to the electrode assembly.

These and other implementations can each optionally include one or more of the following features.

In some implementations, the head covering is attached to the electrode assembly by the electrodes with the second connectors mated to the first connectors.

In some implementations, the first connectors and second connectors are button snaps.

In some implementations, the head covering is made of a washable fabric.

In some implementations, the head covering is made of a disposable fabric.

In some implementations, each electrode includes a base portion that has a larger cross-sectional area than the holes of the head covering.

In some implementations, each electrode includes a plurality of wire electrodes extending therefrom.

In some implementations, the head covering includes a chin strap.

In another general aspect, innovative features of the subject matter described in this specification can be embodied in a method of using an electrode headset that includes actions of obtaining a head covering comprising a plurality of holes, obtaining an electrode assembly comprising a plurality of electrode connectors, aligning the electrode connectors of the electrode assembly with the holes of the head covering, coupling electrodes to the electrode connectors of the electrode assembly through the holes of the head covering thereby securing the head covering to the electrode assembly between the electrodes and the electrode connectors, and placing the head covering over a user's head such that the electrodes are in contact with the user's scalp.

In some implementations the method includes removing the head covering from the user's head, detaching the electrodes and the head covering from the electrode assembly, obtaining a second head covering and second electrodes, coupling the second electrodes to the electrode connectors of the electrode assembly through holes of the second head covering thereby securing the second head covering to the electrode assembly between the second electrodes and the electrode connectors, and placing the clean head covering over a second user's head such that the second electrodes are in contact with the second user's scalp.

In some implementations the method includes disposing of the head covering.

In some implementations the method includes cleaning the electrodes.

In some implementations, the method includes cleaning the head covering.

Particular implementations of the subject matter described in this specification can be implemented so as to realize one or more of the following advantages. Implementations may provide an economical disposable EEG headset system. Implementations may reduce the time needed for EEG set up and cleaning between patients. Implementations provide an EEG headset that can be used for multiple different patients consecutively, while still mainlining cleanliness and sterilization standards.

The details of one or more implementations of the subject matter of this disclosure are set forth in the accompanying drawings and the description below. Other features, aspects, and advantages of the subject matter will become apparent from the description, the drawings, and the claims.

DESCRIPTION OF DRAWINGS

Like reference numbers and designations in the various drawings indicate like elements.

DETAILED DESCRIPTION

In general, this disclosure relates to an electrode headset. The electrode headset can be configured for use with electrical signal analysis systems such as electroencephalogram (EEG) systems and/or other bioamplification systems. The electrode headset includes detachable electrodes that couple a head covering to an electrode assembly. In some examples, the configuration of the electrode headset reduces the amount of maintenance, cleaning, or sterilization required between uses of the headset. For example, the head covering protects the electrode assembly from contact with a user's skin or hair so that it is not necessary to clean or sterilize the electrode assembly between uses. As such, it may not be necessary to disconnect the electrode assembly from an EEG system between uses. In some examples, the head covering is made of a fabric or elastic that is either washable or disposable and can be washed or disposed of between uses. The electrodes that contact a user's hair and skin are detachable, and can be readily replaced with clean electrodes between uses or with different types or sized electrodes. Used (or dirty) electrodes can be cleaned and sterilized when time permits (e.g., between uses).

Figure 1A:
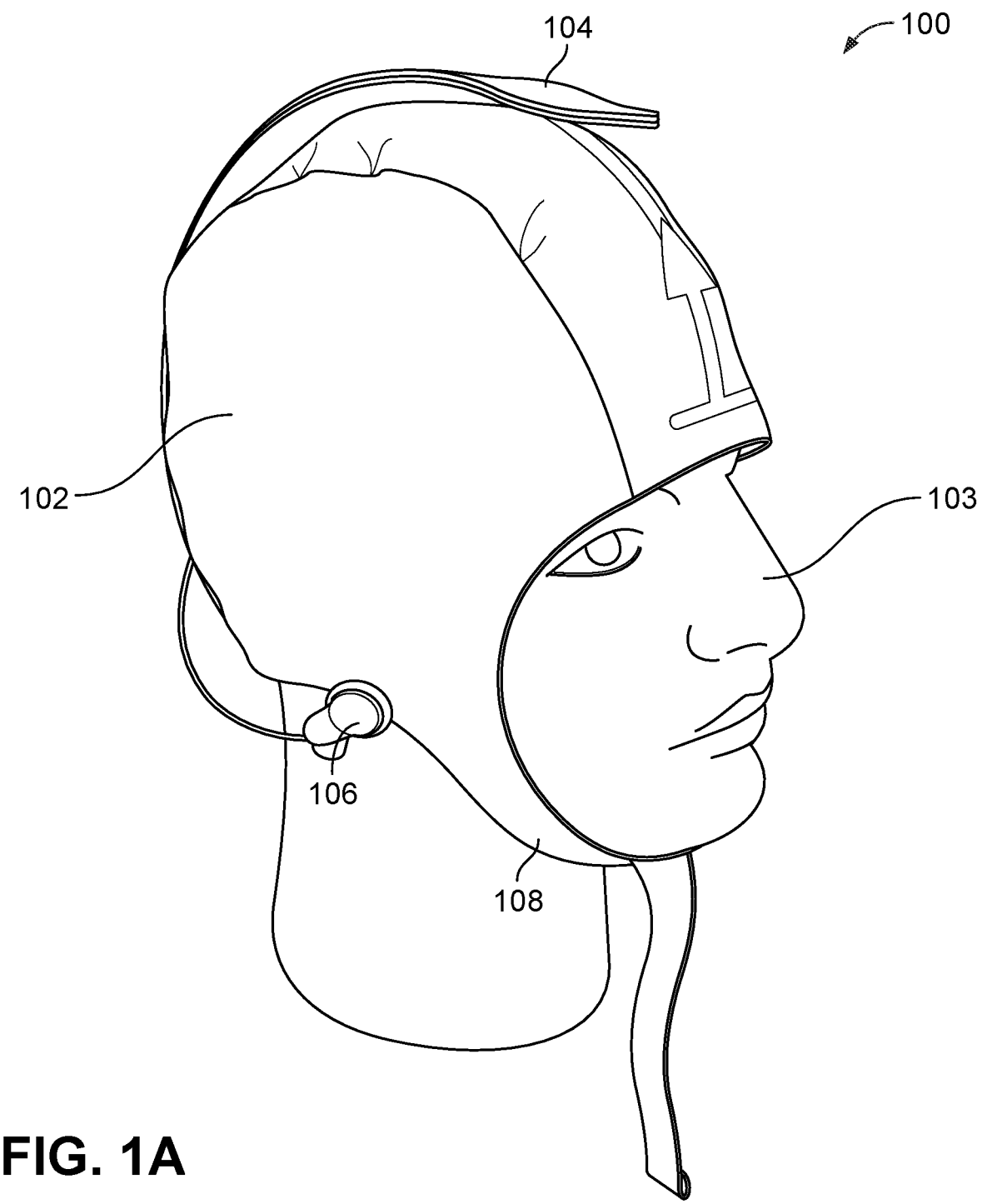
FIG. 1A illustrates a perspective view of an electrode headset according to implementations of the present disclosure.
Figure 1B:
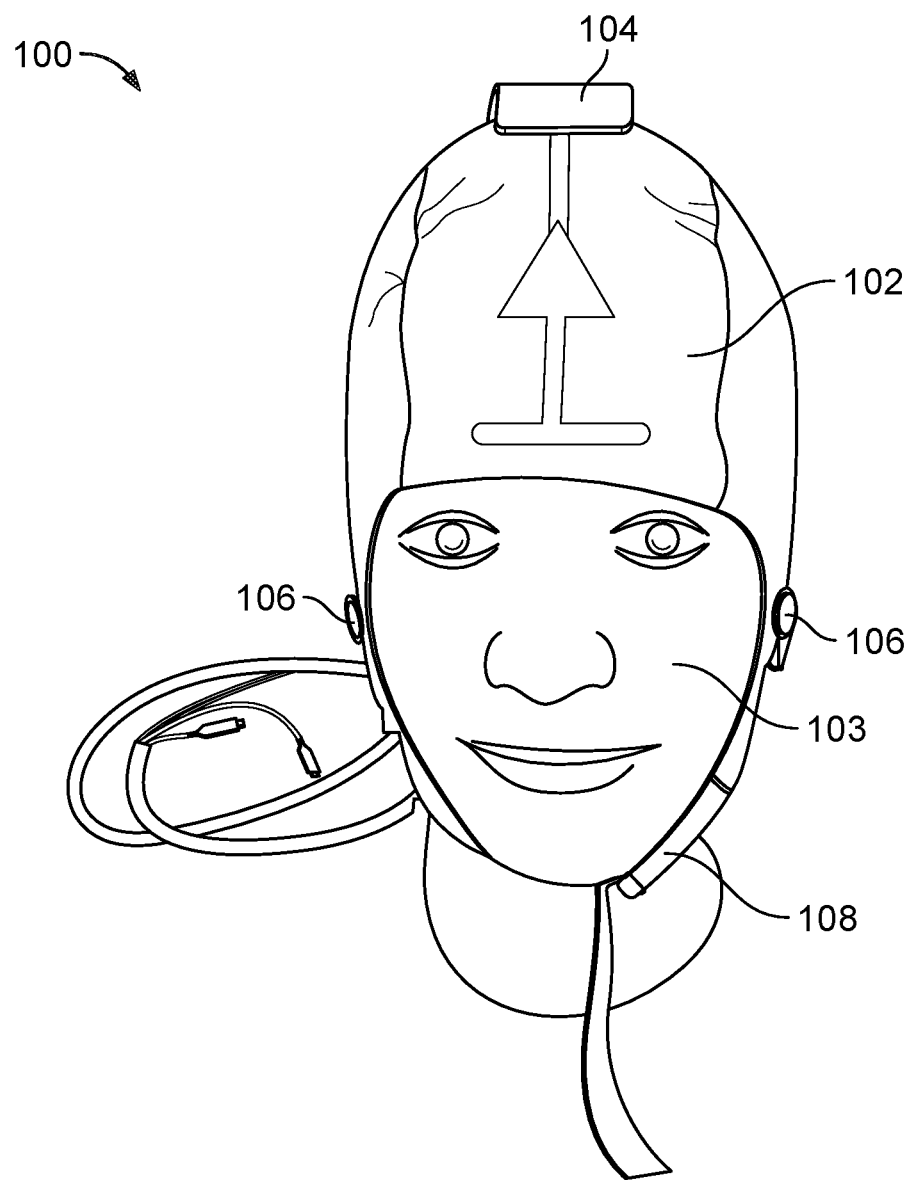
FIG. 1B illustrates a front view of the electrode headset of FIG. 1A.
Figure 1C:
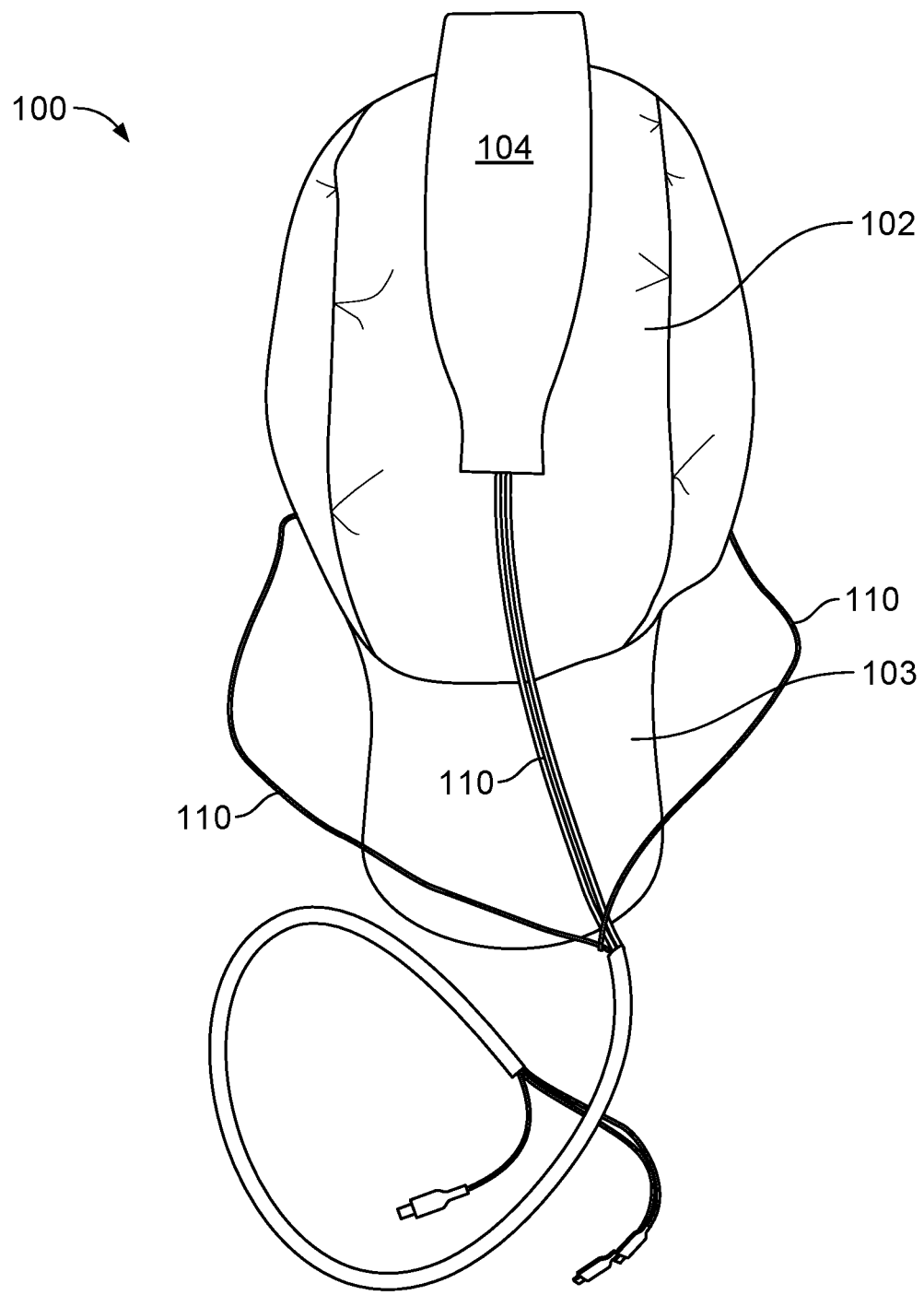
FIG. 1C illustrates a back view of an electrode headset of FIG. 1A.

Referring to FIGS. 1A-1C, the electrode headset 100 includes a head covering 102 and a detachable electrode assembly 104. The head covering 102 is shown as being placed over a user's head 103. For example, the head covering 102 can be made to cover a majority of the user's head 103. In other implementations, the head covering 103 can have a more compact shape/size. The head covering 102 protects the electrode assembly 104 from contact with the user's hair and skin, e.g., to minimize the need for cleaning or disinfecting the electrode assembly 104 between uses. In this way, the electrode assembly 104 may remain connected to an EEG system while changing users, e.g., during clinical research studies. In some examples, the head covering 102 includes a chin strap 108, e.g., to aid in retaining the headset 100 in position on a user's head 103. Furthermore, the head covering 102 (e.g., the chin strap) aids in retaining the electrodes properly positioned with respect to the user's head and/or in contact with the user's skin. In some implementations, the head covering 102 is configured as a "one-size-fits-all" cap. For example, the head covering 102 can be shaped and/or sized to accommodate most, if not all, different user head sizes.

The electrode assembly 104 is attached to the head covering 102 by electrodes (shown in FIGS. 2C and 3) that are positioned on the inside of the head covering 102. The electrodes are shown and explained in more detail below in reference to FIG. 2C. Briefly, the electrodes couple to an underside of the electrode assembly 104 through holes in the head covering 102 and attach the electrode assembly 104 to the head covering 102.

In some examples, the electrode assembly 104 includes ear clips 106 attached to wires that extend out from the electrode assembly 104. Ear clips 106 are configured to attach to a user's earlobes. The ear clips 106 can also include detachable electrodes that contact a user's earlobe when in use, but can be removed and replaced or cleaned between uses. In some implementations, the ear clips 106 can be configured to accept an EKG/EMG sticker-type contact. For example, instead ear clips can be detachable and permit the attachment of a sticker-type electrode contact. Such configurations can be useful when a user has many earings that impede the use of an ear clip. In some implementations, the wires that connect the ear clips to the electrode assembly 104 can be implemented as soft circuits. For example, the wires can be implemented using a textile that includes one or more conductive threads.

Referring to FIG. 1C, the electrode assembly 104 includes several wires 110 extending therefrom that carry electrode signals from the electrodes to an analysis system. For example, an analysis system can be a computing or signal processing system that collects and/or processes electrical signals received by the electrodes such as an EEG system. In some implementations, the electrode assembly 104 can be connected to an analysis system through a wireless network. For example, electrode assembly may include a wireless communication interface for communicating with an analysis system over a wireless network (e.g., a WiFi network, Bluetooth network, etc.).

Figure 2B:
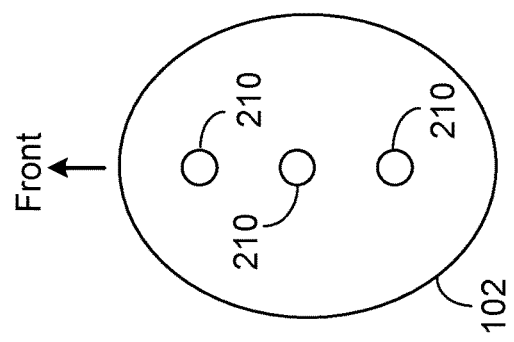
FIG. 2B is a schematic diagram depicting a top view of a head covering of the electrode headset of FIGS. 1A-1C.
Figure 2A:
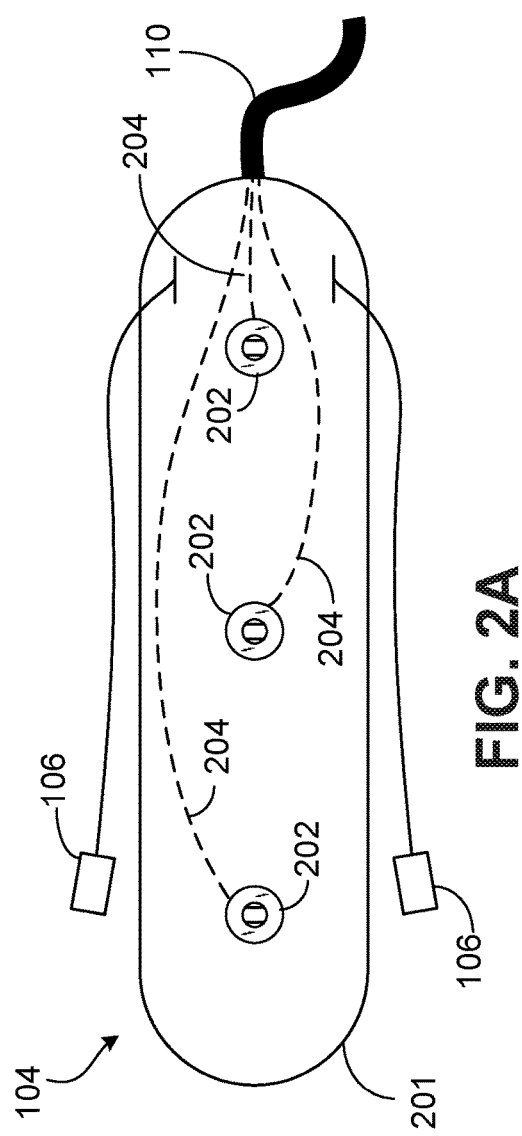
FIG. 2A is a schematic diagram depicting a bottom view of an electrode assembly of the electrode headset of FIGS. 1A-1C.

FIG. 2A is a schematic diagram depicting a bottom view of an electrode assembly 104. Electrode assembly 104 includes a housing 201 that encloses internal components of the electrode assembly 104. The housing 201 can be made of a flexible material or semi-flexible material including, but not limited to, leather, fabric, rubber, or plastic (e.g., a flexible polymer material). Furthermore, the bottom side of the electrode assembly 104 includes electrode connectors 202. The electrode connectors 202 are electrically conductive attachment points configured to mate with a corresponding connector of an electrode (e.g., electrodes 220 shown in FIG. 2C). The electrode connectors 202 can be any appropriate type of releasable mechanical connectors including, but not limited to, button snaps or threaded connectors (e.g. screw-type connectors). The electrode connectors 202 can be fixed in a predetermined arrangement on the bottom side of the housing 201. For example, the electrode connectors 202 can be fixed in a predetermined arrangement that aligns with particular locations on a user's scalp from which EEG measurements are desired.

The electrode assembly housing 201 also encloses internal wires 204 that provide an electrically conductive path from the electrode connectors 202 to the external wiring 110 that is used to interface with an analysis system such as an EEG system. In some implementations, a single housing 201 contains electrode connectors 202 for all of the EEG electrodes that are to be used for a particular type of EEG analysis. In addition, the housing 201 encloses wiring 204 from all of the electrode connectors 202. Such implementations, may reduce the number of parts and external wiring of the headset 100. In some implementations, the wiring for the ear clips 106 can also be bundled within the housing 201, e.g., as illustrated in FIG. 2A.

In some implementations, the electrode assembly housing 201 also contains electronic circuitry associated with the electrode connectors 202. For example, some or all of the electrode connectors 202 can be coupled to respective operational amplifier (op-amp) circuits. More specifically, in some implementations, a unity gain op-amp circuits are integrated into each electrode connector 202.

The electrode assembly 104 can include any number of electrode connectors 202. For example, the electrode assembly 104 can include a number of electrode connectors 202 that are needed or appropriate for measuring specific types or numbers of brain waves. Furthermore, electrode connectors 202 can be arranged on the bottom of the electrode assembly 104 such that when placed on a user's head electrode connectors 202 (i.e., the electrodes coupled to the electric connectors 202) align with appropriate regions of a user's skull in order to measure the desired brain waves. In other words, the size of the electrode assembly, shape of the electrode assembly, number of electrode connectors 202 on the electrode assembly, arrangement of electrode connectors 202 on the electrode assembly 104, or any combination thereof can be modified to position electrodes in appropriate positions with respect to a user skull for measuring a desired set of brain waves.

For example, the electrode connectors 202 on the electrode assembly 104 can be positioned in an arrangement to measure brain waves from regions of the head associated with particular brain systems (e.g., brain systems that provide indications of depression or anxiety in a patient). In some implementations, the electrode connectors 202 can be positioned in an arrangement to measure brain waves from the emotion system (e.g., the amygdala), the visual attentive system (e.g., the visual cortical system V1-V4), and/or the error monitoring system (e.g., anterior cingulate system). In some implementations, the electrode connectors 202 can be positioned in an arrangement to measure brain waves from the risk/reward system (e.g., the dopaminergic brain system) and/or the emotion processing system (e.g., the amygdala).

Figure 5:
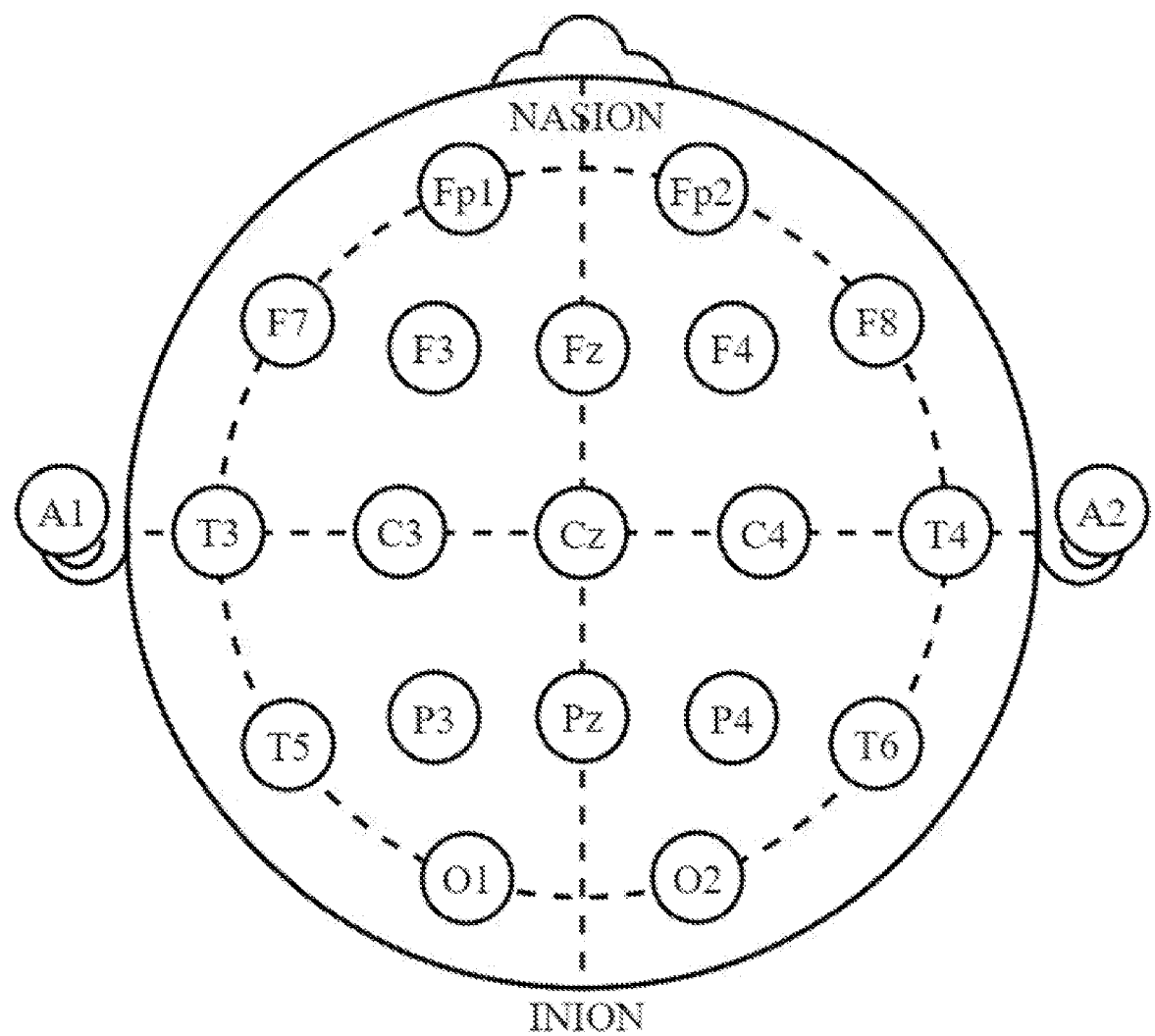
FIG. 5 depicts an EEG electrode layout according to the International 10-20 system.

One example arrangement can include three electrode connectors 202 positioned to contact a user's scalp in the Fz, Cz, and Pz regions of the International 10-20 electrode placement system (depicted in FIG. 5). In some examples, the electrode assembly need only include three electrode connectors 202 positioned to contact a user's scalp in the Fz, Cz, and Pz regions, and no others. In other implementations, the arrangement of electrode connectors 202 on the electrode assembly 104 can include different configurations of between 1 and 256 electrode connectors 202 arranged in a common housing 201. In another example implementation the electrode assembly 104 can include 19-32 electrode connectors 202 arranged according to the 10-20 system arrangement.

FIG. 2B is a schematic diagram depicting a top view of a head covering 102 of the electrode headset 100. The head covering 102 includes several holes 210. The holes 210 are arranged in a pattern similar to that of the electric connectors 202 of the electrode assembly 104. In other words, the holes 210 of the head covering 102 and electric connectors 202 of the electrode assembly 104 are arranged to align with each other so that the electrodes 220 (as shown and described in reference to FIG. 2C) can be coupled to the electrode connectors 202 through the holes 210. In some examples, the head covering 102 can include more holes than electrode connectors 202 on a particular electrode assembly. For example, head coverings 102 can include holes arranged in a pattern that maps to every one of the electrode positions for a 10-20 system electrode arrangement or a 10-10 system electrode arrangement.

Figure 2C:
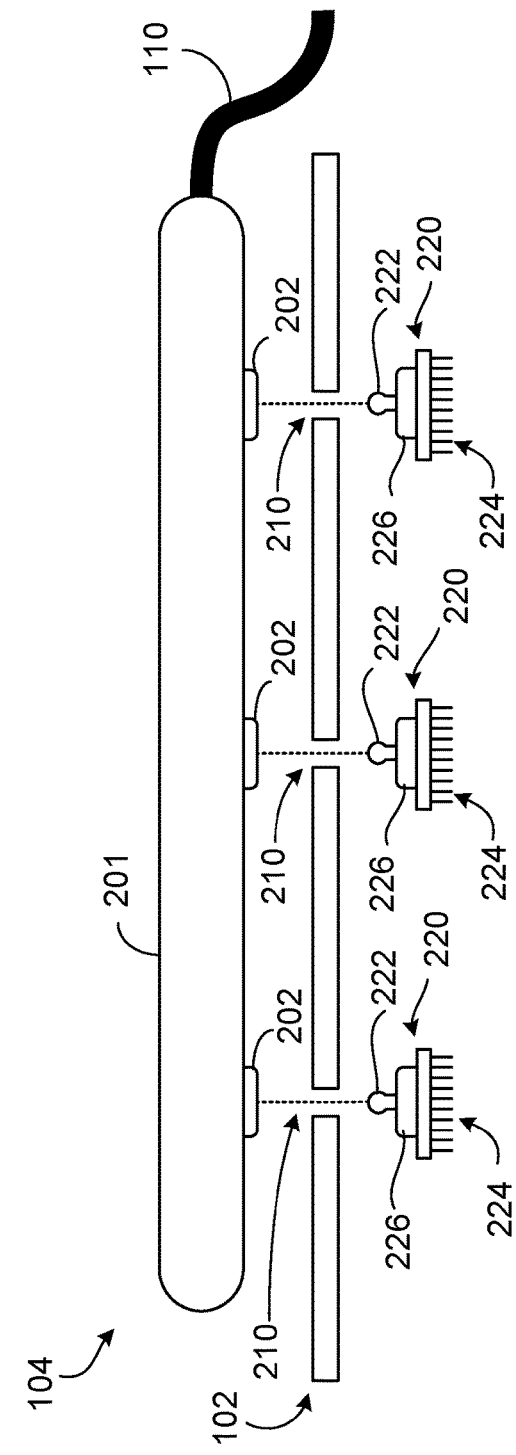
FIG. 2C is a schematic diagram depicting the interconnection between the electrode assembly and the head covering.

FIG. 2C is a schematic diagram depicting the interconnection between the electrode assembly 104 and the head covering 102 of the electrode headset 100. FIG. 2C illustrates how the electrodes 220 couple with the electrode connectors 202 in order to attach the head covering 102 to the electrode assembly 104. For example, electrodes 220 include connectors 222 that are configured to mate with connectors 202 of the electrode assembly 104. When coupled, the connection between connector 202 in connector 222 form a conductive electrical path.

The electrode 220 couples to the electric connector 202 of the electrode assembly 104 through respective holes 210 of the head covering 102. Furthermore, for example, the holes 210 of the head covering 102 are sized such that they allow the respective connectors 202, 222 to mate with each other through the holes 210, but do not permit the entire electrode 220 to pass through the holes 210. When the electrodes 220 are coupled to the electrode assembly 104, the interconnection sandwiches a portion of the head covering 102 in between and retains the head covering 102 in attachment with the electrode assembly 104.

Moreover, head coverings 102 can be provided in a variety of sizes to fit different user head sizes. In such implementations, the distance between the holes 210 in the head covering 102 can be adjusted to each size in order to properly align to a 10-20 or 10-10 arrangement of electrodes for the particular head size. Furthermore, because the electrode assembly 104 is made of a flexible material, when attached to the head covering a standard electrode assembly 104 can flex to adjust to/accommodate the different electrode spacing associated with different head sizes. In other words, as discussed above, the number and arrangement of electrode connectors 202 on an electrode assembly 104 can be arranged for a particular set of desired brain wave measurements in a general manner, and the spacing between holes of different size head coverings 102 arranged in a standard pattern (e.g., 10-20 or 10-10) can serve to provide fine adjustment of electrode positioning as the electrode assembly 104 flexes when attached to the head covering 102 (e.g., in the manner depicted in FIG. 2C).

In some implementations, the electrodes 220 can include a plurality of wire electrodes 224 extending therefrom. The wire electrodes 224 can be configured to pass through a user's hair to contact the user scalp. For example, wire electrodes 224 can be thin comb-like structures. In some examples, the wire electrodes 224 can include a small ball at the tip or a rounded tip to, e.g., avoid scratching the user's scalp. The electrodes 220 can include a base portion 226 that is sized larger than the holes 210 of the head covering 102 (e.g., the base portion 226 can have a cross-sectional area or a diameter that is larger than a corresponding cross-sectional area or diameter of the holes 210). For example, the base portion 226 may aid in capturing and retaining the head covering 102 attached to the electrode assembly 104. In some implementations, the electrodes 220 can include a soft conductive rubber with silver (AG)/silver-chloride (AGCL) coating.

Although the connector 222 on the electrode 220 is illustrated as a male connector and the connector 202 of the electrode assembly 104 is illustrated as a female connector, in some examples, the two types of connectors may be swapped. For example, a male connector may be used as the connector 202 of the electrode assembly 104 and a female connector may be used as the connector 222 on the electrode 220.

Figure 3:
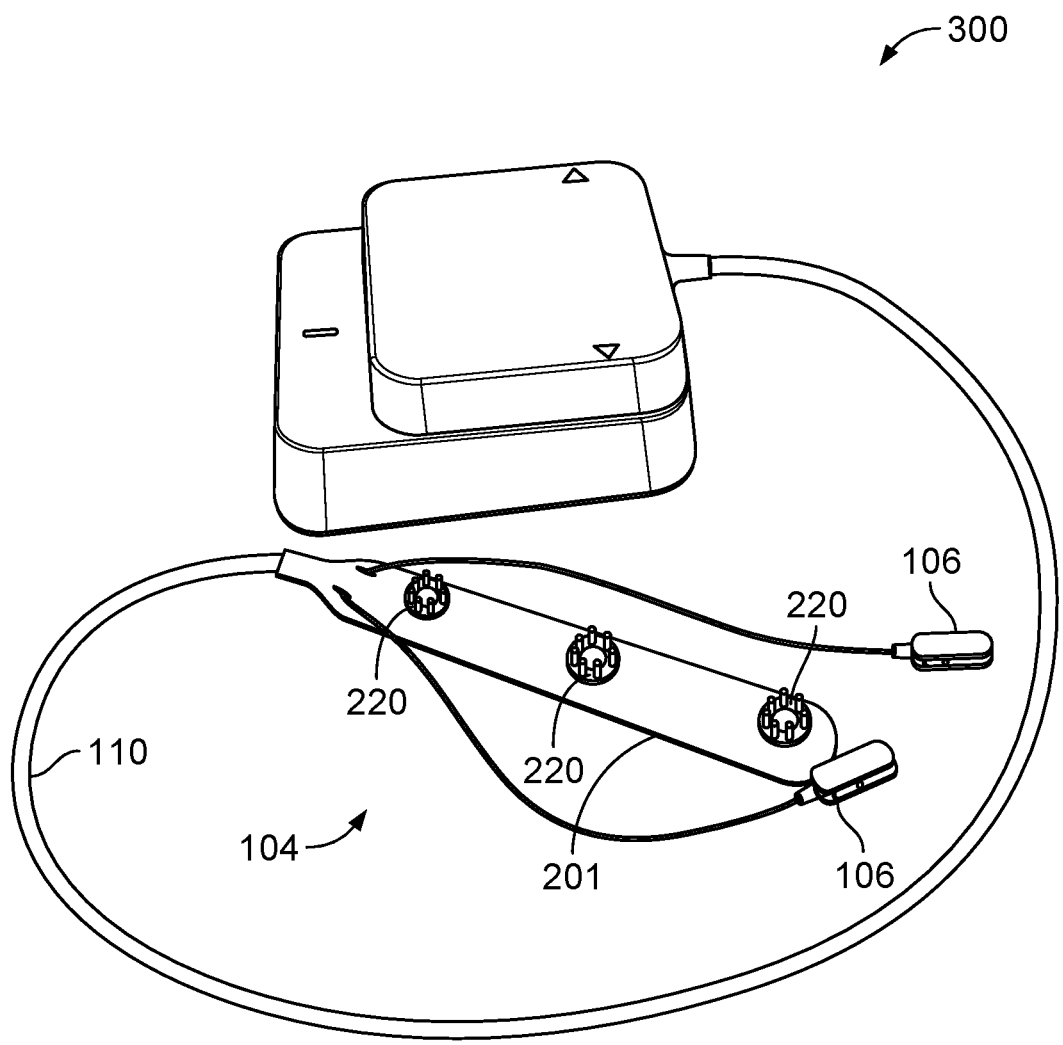
FIG. 3 illustrates the electrode assembly coupled to an analysis system interface device.

FIG. 3 illustrates the electrode assembly 104 coupled to an analysis system interface device 300. The interface device 300 provides a signal interface between the electrodes 220 and an analysis system. For example, the interface device 300 can communicate the electrical brainwave signals measured by the electrodes 220 to an EEG system (e.g., an EEG acquisition or an EEG acquisition and analysis system).

Figure 4:
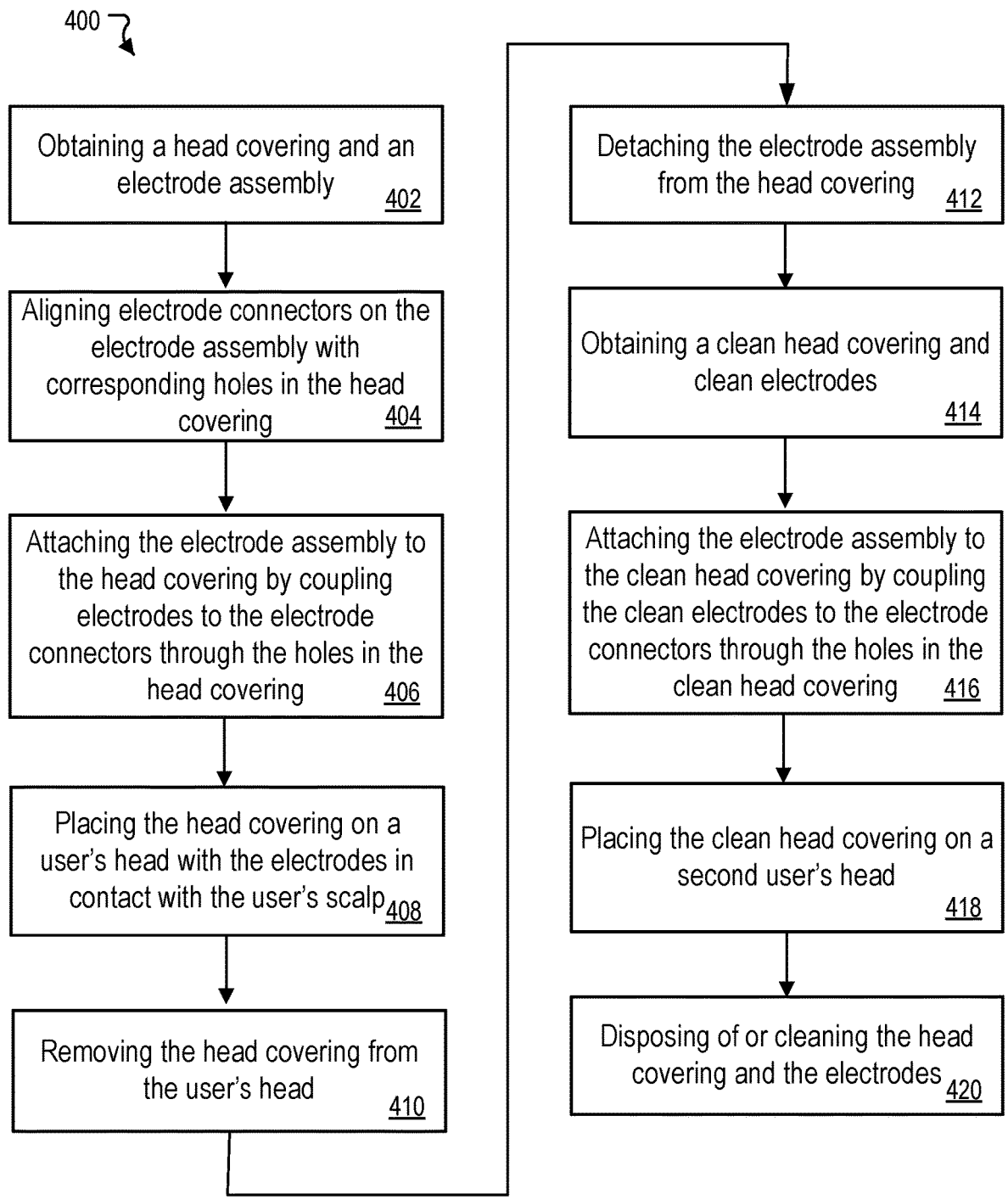
FIG. 4 is a flowchart of an example process for using the electrode headset according to implementations of the present disclosure.

FIG. 4 is a flowchart of an example process 400 for using the electrode headset. Specifically, process 400 provides exemplary processes for assembling and disassembling the electrode headset described above. A head covering and electrode assembly are obtained (402). For example, the head covering 102 and electrode assembly 104 described above are obtained. The electrode assembly 104 is attached to the head covering 102 by aligning the electrode connectors 202 of the electrode assembly 104 with holes 210 of the head covering 102 (404) and coupling electrodes 220 to the electrode connectors 202 of the electrode assembly 104 through the holes 210 of the head covering 102 (406). The head covering 102 is thereby secured to the electrode assembly 104 between the electrodes 220 and the electrode connectors 202. The head covering 102 with the electrode assembly 104 attached is placed a user's head such that the electrodes are in contact with the user's scalp (410). The user's brainwaves can then be monitored by an analysis system through the electrodes.

Once a first user's session is complete, the electrode headset can be removed and prepared for use by another user. For example, the head covering 102 is removed from the first user's head (410). The electrode assembly 104 is detected from the head covering (412). For example, the electrode assembly 104 can be detached by uncoupling the electrodes 220 from the electrode assembly 104 and removing the head covering. A clean (e.g. new or disinfected) head covering 102 and clean (e.g., new or disinfected) electrodes 220 are obtained (414). The clean head covering 102 and clean electrodes 220 are attached to the electrode assembly 104 (416). For example, the clean head covering 102 is attached to the electrode assembly 104 by coupling the clean electrodes 220 to the electrode connectors 202 of the electrode assembly 104 through holes 210 of the clean head covering 102. The clean head covering with the electrode assembly 104 attached is placed over a second user's head such that the second electrodes 220 are in contact with the second user's scalp.

The first head covering 102 and first set of electrodes 220 can be disposed or cleaned/sanitized for use by another user (420). For example, the first head covering 102 can be set aside to be washed at a later time. The electrodes 220 can likewise be set aside for later sterilization or placed directly in a sterilizing solution while the clean set is in use.

While a number of examples have been described for illustration purposes, the foregoing description is not intended to limit the scope of the invention, which is defined by the scope of the appended claims. There are and will be other examples and modifications within the scope of the following claims.

This specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In addition, the processes depicted in the figures do not require the particular order shown, or sequential order, to achieve desirable results. In addition, other steps can be provided, or steps can be eliminated, from the described flowchart. Accordingly, other embodiments are within the scope of the following claims.

What is claimed is:

1. An electrode headset comprising:
   an electrode assembly comprising:
      a flexible housing,
      a plurality of first connectors on one side of the flexible housing, and
      a plurality of wires enclosed within the housing, each wire coupled to one of the first connectors at an end of the first connector that is inside the housing;
   a fabric head covering comprising holes arranged to align with the first connectors of the electrode assembly; and
   a plurality of electrodes, each electrode comprising a second connector configured to releasably mate with one of the first connectors of the electrode assembly through one of the holes of the head covering, wherein respective connections between the electrodes and the connectors capture a portion of the head covering therebetween attaching the head covering to the electrode assembly.

2. The electrode headset of claim 1, wherein the head covering is attached to the electrode assembly by the electrodes with the second connectors mated to the first connectors.

3. The electrode headset of claim 1, wherein the first connectors and second connectors are button snaps.

4. The electrode headset of claim 1, wherein the holes in the head covering are arranged according to a 10-20 electrode placement system.

5. The electrode headset of claim 4, wherein the plurality of first connectors comprise three connectors positioned on the flexible housing to contact a user's scalp in the Fz, Cz, and Pz regions of the 10-20 electrode placement system.

6. The electrode headset of claim 1, wherein each electrode comprises a base portion that has a larger cross-sectional area than the holes of the head covering.

7. The electrode headset of claim 1, wherein each electrode comprises a plurality of wire electrodes extending therefrom.

8. The electrode headset of claim 1, wherein the head covering comprises a chin strap.

9. An electrode headset comprising:
   an electrode assembly comprising:
      a flexible housing,
      a plurality of first connectors on one side of the flexible housing, the plurality of first connectors arranged to align with regions of a user's head that are associated with brain systems that provide indications of depression or anxiety, and
      a plurality of wires enclosed within the housing, each wire coupled to one of the first connectors at an end of the first connector that is inside the housing;
   a fabric head covering comprising holes arranged to align with the first connectors of the electrode assembly; and
   a plurality of electrodes, each electrode comprising a second connector configured to releasably mate with one of the first connectors of the electrode assembly through one of the holes of the head covering, wherein respective connections between the electrodes and the connectors capture a portion of the head covering therebetween attaching the head covering to the electrode assembly.

10. The electrode headset of claim 9, wherein the electrode connectors are button snaps.

11. The electrode headset of claim 9, wherein the flexible housing is made of flexible leather.

12. The electrode headset of claim 9, wherein the flexible housing is made of a flexible polymer material.

13. The electrode headset of claim 9, wherein each electrode comprises a base portion that is sized wider than the holes of the head covering.

14. The electrode headset of claim 9, wherein each electrode comprises a plurality of wire electrodes extending therefrom.

15. The electrode headset of claim 9, wherein the head covering comprises a chin strap.

* * * * *